US008802888B2

(12) United States Patent
Mathe et al.

(10) Patent No.: US 8,802,888 B2
(45) Date of Patent: Aug. 12, 2014

(54) PROCESS FOR THE PREPARATION OF TRANS 4-AMINO-CYCLOHEXYL ACETIC ACID ETHYL ESTER HCL

(75) Inventors: Tibor Bence Mathe, Budapest (HU); Olga Marianna Mathe, legal representative, Budapest (HU); Julia Mathe, legal representative, Budapest (HU); Laszlo Hegedus, Budapest (HU); Laszlo Czibula, Budapest (HU); Balint Juhasz, Torokbalint (HU); Judit Nagyne Bagdy, Budapest (HU); Denes Markos, Esztergom-kertvaros (HU)

(73) Assignee: Richter Gedeon Nyrt., Budapest (HU)

( * ) Notice: Subject to any disclaimer, the term of this patent is extended or adjusted under 35 U.S.C. 154(b) by 656 days.

(21) Appl. No.: 13/140,237

(22) PCT Filed: Dec. 17, 2009

(86) PCT No.: PCT/HU2009/000107
§ 371 (c)(1),
(2), (4) Date: Jul. 28, 2011

(87) PCT Pub. No.: WO2010/070368
PCT Pub. Date: Jun. 24, 2010

(65) Prior Publication Data
US 2011/0288329 A1    Nov. 24, 2011

(30) Foreign Application Priority Data
Dec. 17, 2008  (HU) .................................... 0800762

(51) Int. Cl.
C07C 229/46  (2006.01)
C07C 227/04  (2006.01)
C07C 61/08  (2006.01)
C07C 229/40  (2006.01)

(52) U.S. Cl.
CPC ............... *C07C 229/46* (2013.01); *C07C 61/08* (2013.01); *C07C 229/40* (2013.01); *C07C 227/04* (2013.01)
USPC ........................................................ 560/125

(58) Field of Classification Search
CPC .... C07C 229/46; C07C 61/08; C07C 229/40; C07C 227/04
USPC ............................................................ 560/125
See application file for complete search history.

(56) References Cited

FOREIGN PATENT DOCUMENTS

EP          0224751         10/1987
KR         2005043131        5/2005

OTHER PUBLICATIONS

S. H. Kim, et al., Preparation method of 4-biphenylacetic acid with high yield and high purity, Database WPI Week 200648, Thomson Scientific, London AN 206-468774, XPO-02581633.
Wustrow, et al., Aminopyrimidines with High Affinity for Both Serotonin and Dopamine Receptors, J. Med. Chem. 1998, 41, pp. 760-771.
EPO Search Report dated May 10, 2010, mailed May 27, 2010, Authorized Officer Marielle Seelmann.

*Primary Examiner* — Yevegeny Valenrod
(74) *Attorney, Agent, or Firm* — Fish & Richardson P.C.

(57) ABSTRACT

The invention relates to a process for the preparation of trans 4-amino-cyclohexil ethyl acetate HCl wherein
d) hydrogenating 4-nitrophenyl acetic acid in a protic solvent at a temperature between 40-50° C. in the presence of Pd/C under 0.1-0.6 bar overpressure, and
e) further hydrogenating the 4-aminophenyl acetic acid obtained in situ in step a) at a temperature between 50-60° C. under 1-4 bar overpressures, then
f) heating to reflux the 4-aminocyclohexil acetic acid obtained in step b) for 1-3 hours in hydrochloric ethanol, and if desired after removing the solvent acetonitrile was added to the residue obtained and distilled off.

4 Claims, No Drawings

PROCESS FOR THE PREPARATION OF TRANS 4-AMINO-CYCLOHEXYL ACETIC ACID ETHYL ESTER HCL

CROSS-REFERENCE TO RELATED APPLICATIONS

This application is a National Stage application under 35 U.S.C. §371 of International Application No. PCT/HU2009/000107, having an International Filing Date of Dec. 17, 2009, which claims the benefit of priority of HU Application No. P08 00762, having a filing date of Dec. 17, 2008, all of which are incorporated herein in their entirety.

FIELD OF THE INVENTION

The present invention relates to a new process for the preparation of trans 4-amino-cyclohexyl acetic acid ethyl ester HCl.

BACKGROUND OF THE INVENTION

The trans 4-amino-cyclohexyl acetic acid and its derivatives are excellent starting materials for the synthesis of active pharmaceutical agents, therefore it is important to provide an economical process by which the trans 4-amino-cyclohexyl acetic acid and its derivatives can be prepared easy-to-make manner in the required drug-purity and with good yields. For the synthesis of active pharmaceutical agents only the optical (stereomerically) pure trans isomer form may be applicable.

Izvesztiya Akademii Nauk SSSR, Seriya Khimicheskaya (10), 2374-9 (Russian) 1980 discloses a process for the preparation of cis and trans isomers of 4-amino-cyclohexyl acetic acid and their derivatives. Accordingly, cis and trans isomers of 4-amino-cyclohexyl acetic acid are obtained starting from 4-nitrophenylacetic acid sodium salt by a hydrogenation reaction at 130° C. and 150 at pressures in the presence of Raney-Ni catalyst. The products obtained are isolated in the form of hydrogen chloride salts.

According to Wustrow at al (Journal of Medicinal Chemistry, 1998 vol. 41 No. 5 768.) trans 4-amino-cyclohexyl acetic acid ethyl ester hydrogen chloride salt is obtained from 4-nitrophenyl acetic acid by hydrogenation. The hydrogenation of a sodium salt is carried out at first in an aqueous medium in the presence of Raney-Ni catalyst at 49° C. and under 130 at pressures, then further at 130° C. and under 172 at pressures. The 4-amino-cyclohexyl-acetic acid obtained consists of about 81% of trans and 19% of cis isomers. Isolation of the required trans isomer is difficult to manage, as the mixture of the isolated trans and cis 4-amino-cyclohexyl acetic acid is dissolved in ethanol and saturated with anhydrous hydrochloric acid gas and heated to reflux. After cooling the mixture is filtered, the filtrate obtained is concentrated and the trans product is precipitated by ether.

The common disadvantages of the above known procedures are e.g. that the processes can be carried out only at very high temperatures and pressures in the presence of the very pyrophoric Raney-Ni catalyst therefore the industrial procedures are uneconomical and dangerous and require extra equipments and extreme conditions. Further disadvantage is that a sodium salt is hydrogenated therefore the working-up and recovering steps are difficult to manage. Namely, the trans 4-amino-cyclohexyl acetic acid ethyl ester hydrochloric acid salt is produced in anhydrous conditions in ethanol, saturated with hydrochloric acid in addition the reaction mixture is heated to reflux and the product is precipitated with ether. The procedure is disadvantageous from environmental point of view due to use of the very corrosive hydrochloric acid and inflammable ether. Our aim was to provide a safe and easy-to-handle process for the preparation of trans 4-amino-cyclohexyl acetic acid or well isolable derivatives thereof in industrial scale by which the product can be prepared via simple reaction steps and besides that said steps require neither solvents that are highly flammable and/or corrosive nor extra equipments.

DETAILED DESCRIPTION OF THE INVENTION

We have surprisingly found that when 4-nitrophenyl acetic acid is hydrogenated in an aqueous medium in the presence of Pd/C, at 3-4 bar overpressure—which can be made easily in a common autoclave—a mixture of cis/trans 4-amino-cyclohexylacetic acids is obtained wherein the ratio of cis product to trans is approx. 70%. Our investigations increasing the trans-selectivity surprisingly showed that when the hydrogenation is performed in the presence of Pd/C, in two reaction steps—namely, when reduction of the nitro group and saturation of the phenyl ring are carried out in separate steps—the trans selectivity is increased. When reduction of the nitro group is performed at a temperature between 40-50°, preferably at 44-46° C. and at least 0.6 bar overpressure, the phenyl group remains unreacted, then the 4-aminophenyl acetic acid obtained in situ is further hydrogenated at a temperature between 50-60° C., preferably at 55-58° C. and at least 4 bar overpressure. In this case the trans →cis ratio becomes more advantageous and the conversion of trans isomer is reaches 60-70%. Besides, we have found that carrying out the hydrogenation of 4-nitrophenyl acetic acid in free acid form, in a protic solvent, for example in water, methanol, ethanol, propanol, or in a mixture thereof, preferably in water, all two hydrogenation steps can be proceed. Using the said conventional procedures separation and purification of cis and trans cyclohexyl acetic acids can be carried out only with law efficiency and hard-to make manner. But we have surprisingly found, that when cyclohexyl acetic acid alkyl ester derivatives, for example methyl, ethyl, propyl ester derivatives are prepared, the mixture of cis/trans ethyl ester hydrochloric acids can be separated to trans and cis products with good trans yield. A known general method for esterification of amino acids is to dissolve the amino acids in an esterifying alcohol and to add thionylchloride, wherein the amino acid esters are obtained without side products. According to the above known processes the ethyl ester HCl salt is produced in anhydrous medium saturated with hydrochloride gas and the very flammable ether solvent is added to precipitate the end product.

We have surprisingly found that when the preparation of trans 4-amino-cyclohexyl acetic acid ethyl ester is performed in ethanolic medium using hydrochloric acid in en excess of 10-30, preferably 20 mol %, the end-product is formed in equimolar amount without forming side-products. Another advantage of the process according to the invention that there is no need for anhydrous reaction conditions therefore the water content of the medium can reaches 15 v % of the starting volume of 4-nitrophenyl acetic acid.

Besides we have surprisingly found that when the cis/trans mixture of 4-aminocyclohexyl acetic acid ethyl ester HCl salt prepared according to the invention is treated with acetonitrile, the trans product can be isolated in extremely high purity and good yield.

The present invention relates to a process for the preparation of trans 4-amino-cyclohexyl acetic acid ethyl ester HCl wherein the process comprises the following steps:

step 1: 4-nitrophenyl acetic acid is hydrogenated in a protic solvent in the presence of Pd/C, at a temperature between 40-50° C. and under 0.1-0.6 bar overpressure;

step 2: the 4-amino-nitrophenyl acetic acid obtained in situ in step 1 is further hydrogenated at a temperature between 50-60° C. and under 1-4 bar overpressures;

step 3: the 4-amino-cxyclohexyl acetic acid obtained in step 2 is heated to reflux in hydrochloric ethanol for 1-3 hours and after removing the solvent by distilling in vacuum acetonitrile is added to the residue obtained and distilled off. The distillate is cooled to a temperature between −5-0° C. and the crystals precipitated is washed with acetonitrile.

The invention is illustrated by the following non-limiting Example.

EXAMPLE

Preparation of trans 4-amino-cyclohexyl-acetic acid ethyl ester HCl

A 2500 l enamelled autoclave is charged with 1000 kg of deionizated water and 210 kg (1.16 kM) of 4-nitrophenyl-acetic acid at room temperature under nitrogen atmosphere. After inertisation by nitrogen to the mixture obtained a suspension of 21 kg of 10% Pd/C in 20 kg of deionized water is added and the catalyst measuring gauge is rinsed by additional 20 kg of deionized water. After rinsing the reaction vessel by hydrogen gas the hydrogenation is carried out at a temperature between 44-46° C. and under up to 0.6 bar overpressure until the hydrogen uptake is slowed. After reducing the nitro group the temperature is brought to 55-58° C. and the hydrogenation continued maintaining hydrogen pressure on max. 4.0 bar overpressures. After completion of the hydrogen uptake, the mixture is cooled to a temperature between 25-30° C., purged with nitrogen and the catalyst is filtered on a Spakler filter under pressurized nitrogen. The reaction vessel, the filter and the lines are washed additional 200 g of deionized water. The filtrates are combined and in a 2500 l enamelled doubler 1200 kg of distillate is distilled at up to 80° C. inner temperature in vacuum. The residue obtained is cooled to a temperature below 30° C. and 430 kg of ethyl alcohol is added, then 500 l of distillate is collected at up to 80° C. under vacuum.

After completion of the distillation the mixture is cooled to a temperature between 25-30° C., (water content is max. 10 w %, in terms of absolute value is about 32 kg), and 550 kg of ethyl alcohol, then 170 kg of 30% hydrochloric ethyl alcohol are added and the reaction mixture is heated to reflux for approx. 2 hours. When the esterification is complete 800 l of solvent is distilled off at up to 80° C., under vacuum. Additional 800 l of ethyl alcohol is added and further 750-800 l of solvent is distilled off at up to 80° C., under vacuum. To the residue obtained 700 kg of acetonitrile is added and 140 l of distillate is collected at up to 80° C. under vacuum. The vacuum is stopped by introducing nitrogen and the solution is cooled to a temperature between 0-(−)5° C. The crystals obtained is centrifuged, washed with 100 kg of acetonitrile in two portions during which the temperature is kept at 0-(−)5° C. The solid obtained is dried to a constant weight at up to 60° C.

In this manner 90 kg of title product is obtained.

Yield: 40%.

Melting point: 173-176° C.

The invention claimed is:

1. Process for the preparation of trans 4-amino-cyclohexil ethyl acetate HCl comprising
   a) hydrogenating 4-nitrophenyl acetic acid in a protic solvent at a temperature between 40-50° C. in the presence of Pd/C under 0.1-0.6 bar overpressure, and
   b) further hydrogenating the 4-aminophenyl acetic acid obtained in situ in step a) at a temperature between 50-60° C. under 1-4 bar overpressures, then
   c) heating the 4-aminocyclohexil acetic acid obtained in step b) to reflux for 1-3 hours in hydrochloric ethanol, and optionally after removing the solvent, acetonitrile is added to the residue obtained and then distilled off.

2. Process according to claim 1 characterized in that as a solvent water is employed.

3. Process according to claim 1 characterized in that in step a) the hydrogenation is carried out at a temperature between 44-46° C.

4. Process according to claim 1 characterized in that in step b) the hydrogenation is carried out at a temperature between 55-58° C.

* * * * *

UNITED STATES PATENT AND TRADEMARK OFFICE
CERTIFICATE OF CORRECTION

PATENT NO. : 8,802,888 B2  
APPLICATION NO. : 13/140237  
DATED : August 12, 2014  
INVENTOR(S) : Olga Marianna Mathe et al.

Page 1 of 1

It is certified that error appears in the above-identified patent and that said Letters Patent is hereby corrected as shown below:

ON THE TITLE PAGE

First Page, Column 2, line 2 (Abstract), please delete "4-amino-cyclohexil" and insert -- 4-amino-cyclohexyl --, therefor;

First Page, Column 2, line 9 (Abstract), please delete "4-aminocyclohexil" and insert -- 4-aminocyclohexyl --, therefor;

IN THE CLAIMS

Column 4, line 22, approx. (Claim 1), please delete "4-amino-cyclohexil" and insert -- 4-amino-cyclohexyl --, therefor;

Column 4, line 30, approx. (Claim 1), please delete "4-aminocyclohexil" and insert -- 4-aminocyclohexyl --, therefor.

Signed and Sealed this  
Twenty-sixth Day of January, 2016

Michelle K. Lee  
*Director of the United States Patent and Trademark Office*